US009615846B2

(12) United States Patent
Prestel (10) Patent No.: US 9,615,846 B2
(45) Date of Patent: Apr. 11, 2017

(54) ENDOSCOPIC INSTRUMENT (71) Applicant: RICHARD WOLF GMBH, Knittlingen (DE)

(72) Inventor: Stephan Prestel, Rheinstetten (DE)

(73) Assignee: RICHARD WOLF GMBH, Knittlingen (DE)

( * ) Notice: Subject to any disclaimer, the term of this patent is extended or adjusted under 35 U.S.C. 154(b) by 126 days.

(21) Appl. No.: 14/415,277

(22) PCT Filed: Jul. 1, 2013

(86) PCT No.: PCT/EP2013/063865
§ 371 (c)(1),
(2) Date: Jan. 16, 2015

(87) PCT Pub. No.: WO2014/012780
PCT Pub. Date: Jan. 23, 2014

(65) Prior Publication Data
US 2015/0127045 A1 May 7, 2015

(30) Foreign Application Priority Data
Jul. 17, 2012 (DE) ........................ 10 2012 212 510

(51) Int. Cl.
*A61B 17/29* (2006.01)
*A61B 34/00* (2016.01)
*A61B 34/30* (2016.01)

(52) U.S. Cl.
CPC .............. *A61B 17/29* (2013.01); *A61B 34/30* (2016.02); *A61B 34/71* (2016.02); *A61B 2017/2927* (2013.01); *A61B 2017/2929* (2013.01); *A61B 2017/2933* (2013.01); *A61B 2017/2938* (2013.01); *A61B 2017/2939* (2013.01); *A61B 2017/2947* (2013.01)

(58) Field of Classification Search
CPC ............ A61B 17/29; A61B 2017/2927; A61B 2017/2929; A61B 2017/2933; A61B 2017/2938; A61B 2017/2939; A61B 34/71
See application file for complete search history.

(56) References Cited

U.S. PATENT DOCUMENTS

| 5,562,702 | A | 10/1996 | Huitema et al. |
| 5,792,135 | A * | 8/1998 | Madhani .......... A61B 17/00234 606/1 |
| 6,206,903 | B1 | 3/2001 | Ramans |
| 6,312,435 | B1 | 11/2001 | Wallace et al. |

(Continued)

FOREIGN PATENT DOCUMENTS

WO 2010/005657 A2 1/2010

*Primary Examiner* — Alexander Orkin
(74) *Attorney, Agent, or Firm* — McGlew and Tuttle, P.C.

(57) ABSTRACT

An endoscopic instrument includes a shank (2) with an instrument head (9) arranged at the distal shank end (1) and includes a tool with two jaw parts (11, 12). The jaw parts (11, 12) are pivotable relative to one another and can be controlled from the proximal instrument end via a pull elements (5-8) led in the shank (2). At least one jaw part (11, 12) includes two curved disks (36, 37), on which the pull elements (5-8) engages in each case. Two curved disks (36, 37) of a different radial size are provided for each jaw part (11, 12). The radially larger curved disk is arranged closer to the longitudinal middle axis (14) of the tool than the radially smaller curved disk.

3 Claims, 9 Drawing Sheets

(56) References Cited

U.S. PATENT DOCUMENTS

| | | |
|---|---|---|
| 6,371,952 B1 | 4/2002 | Madhani et al. |
| 6,394,998 B1 | 5/2002 | Wallace et al. |
| 2003/0135204 A1 | 7/2003 | Lee et al. |
| 2007/0208375 A1 | 9/2007 | Nishizawa et al. |
| 2007/0255109 A1* | 11/2007 | Stein ................ A61B 1/00087 600/214 |
| 2007/0288044 A1* | 12/2007 | Jinno .................... A61B 17/29 606/174 |
| 2008/0087871 A1* | 4/2008 | Schena ................. B25J 9/1045 254/226 |
| 2011/0106145 A1 | 5/2011 | Jeong |
| 2012/0158013 A1 | 6/2012 | Stefanchik et al. |

* cited by examiner

ENDOSCOPIC INSTRUMENT

CROSS REFERENCE TO RELATED APPLICATIONS

This application is a United States National Phase Application of International Application PCT/EP2013/063865 filed Jul. 1, 2013 and claims the benefit of priority under 35 U.S.C. §119 of German Patent Application DE 10 2012 212 510.8 filed Jul. 17, 2012, the entire contents of which are incorporated herein by reference.

FIELD OF THE INVENTION

The invention relates to an endoscopic instrument with a shank and with an instrument head, which is arranged at the distal shank end and which comprises a tool with two jaw parts which are pivotable to one another and which can be controlled from the proximal instrument end via a pull elements led in the shank, wherein at least one jaw part comprises two curved disks, each of which is engaged by a pull element.

BACKGROUND OF THE INVENTION

Endoscopic instruments of this type, which comprise an instrument head with a tool having two jaw parts pivotable to one another, are applied nowadays in a comprehensive manner, for example as scissors, forceps or likewise. Thereby, the movement of the jaw parts is effected by way of control from the proximal end of the instrument, either manually via a handle or robotically, i.e. by way of a suitable control device.

Such instruments are known for example from U.S. Pat. Nos. 6,312,435 B1, 6,371,952 B1 , 6,206,903 B1, US 2007/0208375 A1, US 2011/0106145 A1, US 2012/0158013 A1 or WO 2010/005657 A2.

An essential criterion for the application is the shank diameter, irrespective of whether these are robotically actuated, i.e. with electromotoric activation, or however manually activated. The smaller the shank diameter, the more versatile is the application of the instrument, and this instrument can be led to the field of operation through narrow openings which are either natural or which are created by the operator.

One disadvantage of thin shank diameters and, entailed by this, as a rule also thinner instrument heads is the fact that with regard to design, it is difficult to muster the necessary forces in the tool by way of actuation at the proximal end, and this is the case to an increased extent if the instrument head is to be pivotable with respect to the shank, which is often necessary.

SUMMARY OF THE INVENTION

Against this state of the art (US 2012/0158013 A1), it is an object of the invention, to design an endoscopic instrument of the known type, such that on the one hand a small as possible shank diameter can be realized, but on the other hand the forces to be transmitted onto the tool, in particular onto the jaw parts are as high as possible. Moreover, the instrument should be simple in construction and inexpensive in manufacture.

The endoscopic instrument according to the invention comprises a shank, at whose distal end an instrument head is attached, said instrument head comprising a tool with preferably two jaw parts which are pivotable to one another. A pull means can be controlled within the shank from the proximal instrument end. Each jaw part comprises two curved disks (cam discs), onto which the pull means engages in each case. According to the invention, two curved disks of a different radial size are assigned to each jaw part. The radially larger curved disk in each case is arranged closer to a longitudinal middle axis of the tool than the radially smaller curved disk.

The basic concept of the solution according to the invention is to apply curved disks of different radial sizes and thereby to arrange the radially larger curved disks centrally close to the tool axis, and the radial smaller one further to the outside, in order in this manner, as much as possible to also optimally utilise the round shank cross section which as a rule also continues in the tool head. Thereby, the radial distance of the curved disk to the rotation axis is decisive for the force to be applied onto the respective jaw part, since this with a given force determines the moment with which the jaw part can be moved. The maximal closure force is determined by way of this in the case of a forceps, and the shear force in the case of a scissors. By way of the arrangement according to the invention, one succeeds in a larger force being able to be applied in one pivot direction of a jaw part, than in another direction and specifically where the radially larger curved disk is applied. As to the direction, in which this force is to be applied, depends essentially on the application purpose. If, for example, a cavity is to be held open or spread with the jaw parts, then it is useful to provide the radially larger curved disk for pivoting the jaw parts into the open position. In contrast, with a forceps or scissors, usefully the higher force is required in the closure direction, which is why it is then advantageous to assign the radially large curved disks to the pull means which move the jaw parts to one another.

With the previously described, preferred solution according to the invention, with which two curved disks are assigned to each jaw part, apart from the closure and opening of the jaw parts, a pivot movement can also be realized, which provides an addition degree of freedom if both jaw parts are simultaneously pivoted in the same direction.

It is to be understood that the principle according to the invention in the simplest form can be realized with a pivotable jaw part and a further stationary jaw part, and then two curved disks are provided for the pivotable jaw part, specifically a radially larger curved disk which is arranged close to the longitudinal middle axis or in the region of the longitudinal middle axis of the tool, and a radially smaller curved disk which is arranged next to this, where less space is available within the shank cross section.

It is advantageous with tools such as forceps, scissors and likewise, which must muster their greatest force in the closure direction, if the radially larger curved disks are assigned to the pull means for closure, and the radially smaller curved disks are assigned to the pull means for opening the jaw parts. The opening forces as a rule can be a multiple smaller than the necessary closure forces, which is why small levers, i.e. small diameters of the curved disk are sufficient here, in order to muster the necessary forces. These curved disks, on which the pull means for opening the jaw parts are arranged, can have a comparatively small diameter and thus be arranged further to the outside, whereas the radially larger curved disks, thus those whose curve path has a greater radial distance to the rotation axis, are arranged close to the centre, where the greatest free space is given, with the common round or oval instrument diameters.

The shape of the curved disks is basically freely selectable. Thus for example the force at the jaw part can be increased in a targeted manner in certain positions by way of an elliptical curved disk. This can be useful for example if only one jaw part is pivotably movable, in order to achieve the greatest force directly before or in the closure position. With the preferred design, with which both jaw parts are pivotable in both directions and thus realise a further degree of freedom of the endoscopic instrument, it is useful and advantageous to design the curved disks in a circular manner and preferably to arrange them with the circle middle point on the common pivot axis of the jaw parts. Such an arrangement, with a given force on the pull means always ensures the same moment on the jaw part independently of the pivot position, which is basically advantageous.

Radial size in the context of the present invention is to be understood as the maximal radial distance of the curved disk from its rotation point. I.e. the larger curved disk is always that one which has the greatest radial distance to its rotation point, even if this is possibly narrow or in part regions has a smaller radial distance than the other curved disk. The maximal radial distance determines the necessary free space which is required for the arrangement of the curved disk. Here, according to the invention, the larger curved disk is to be arranged in the longitudinal middle axis or close to the longitudinal middle axis and the smaller one further to the outside next to this.

Advantageously, according to a further development of the invention, the pull means are not fixed around the curved disks in a peripheral manner but at the end side, and have an angle of wrap of advantageously more than 90°. The wrap angle of more than 90° ensures that the respective jaw part is also pivotable by an angle of 90° or more, which is advantageous. It is particularly favorable with regard to design, if a jaw part is designed as one piece with the two associated curved disks. On the one hand, the necessary moment transmission is ensured by way of this, and on the other hand such a component can be manufactured inexpensively with a molding/casting method or other shaping method.

Thereby, it is particularly advantageous if the two jaw parts are designed identically, as is advantageously described in the embodiment example further below. Such a design has the advantage that the tool can be constructed with two identical components, which reduces the manufacturing costs and the storage effort.

According to one advantageous further development of the invention, an intermediate piece, in which the jaw parts are mounted and which forms part of the instrument head and is pivotably arranged at the distal shank end is provided, in order to give the instrument a further degree of freedom with regard to the movability of the instrument head. Such an intermediate piece can either further increase the pivotability of the jaw parts if for example the pivot axis of the intermediate piece is parallel to the pivot axis of the jaw parts. However, as a rule, it would be particularly advantageous if the pivot axis of the intermediate piece is arranged at a distance and transversely to the pivot axis of the jaw parts, by which means a pivot movement of the instrument head transversely to the pivot axis of the tool is possible, which increases the degrees of freedom with the movement of the tool head and thus improves the versatility of the instrument with its use.

Advantageously, according to a further development of the invention, one envisages the intermediate piece being constructed from a base body, from which two limbs distanced to one another and receiving the jaw parts with their pivot extend distally, and from which two limbs distanced to one another and receiving the pivot of the intermediate piece and the components arranged thereon extend in the axis direction offset by 90° thereto. Thereby, the base body typically has a circularly round outer contour which advantageously corresponds to the shank contour, whereas the limbs, following the shank contour, locate in each case on two locations close to the outer periphery of the base body which are offset by about 180°.

It is advantageous if the proximally directed limbs of the intermediate piece are connected in a rotationally fixed manner to a shaft, on which in turn a curved disk is arranged in a rotationally fixed manner, on which curved disk pull means for the control of the pivot position of the intermediate piece and leading through the shank to the proximal instrument end engage, in order to be able to control the intermediate piece in its pivot movement with respect to the instrument shank. Thereby, one or two curved disks can be connected to the shaft, depending on whether a curved disk is to be provided for each pull means or, as is particularly advantageous, both pull means engage on a curved disk which can then be arranged centrally within the region of the longitudinal axis, in which region the greatest free space is given on account of the cross sectional contour.

It is advantageous to arrange a deflection roller pair in a rotatably mounted manner between the proximally directed limbs for each pull means leading to a jaw part, and specifically such that one of the deflection rollers is arranged on the shaft whose axis forms the pivot axis of the joint, and the other is arranged offset thereto between the shaft and the base body, in order to lead the pull means for movement of the jaw parts through the joint on the instrument head. Such a deflection roller guidance is particularly favorable for the force transmission, since the force which is mustered by the pull means can be transmitted with little loss through the joint to the jaw parts. Such a roller guidance is always lower in friction than e.g. a Bowden cable arrangement. It can moreover be applied over pivot regions extending beyond 90°.

A particularly advantageous further development of the instrument according to the invention results if each deflection roller pair is arranged such that the wrap angle of the associated pull means around the deflection roller pair is independent of the pivot position of the intermediate piece. A pivoting of the intermediate piece, i.e. a pivoting of the instrument head with respect to the instrument shank then has no influence whatsoever on the tool movement and the tool forces. This is particularly advantageous with a manual actuation of the instrument, but also with a robotic connection, since a movement compensation demanding computation and motor capacity is not necessary.

The invention is hereinafter explained in more detail by way of one embodiment which is represented in the drawing.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

With regard to the endoscopic instrument according to the invention, only the distal instrument part is hereinafter described and represented. The longitudinally extended shank as well as the proximal design, be it as a handle for the direct manual actuation by the operator or as a robotic connection as is known with the instrument known from U.S. Pat. No. 6,312,435 B1 is counted as belonging to the general state of the art and is not the subject matter of the present invention.

Figure 1:
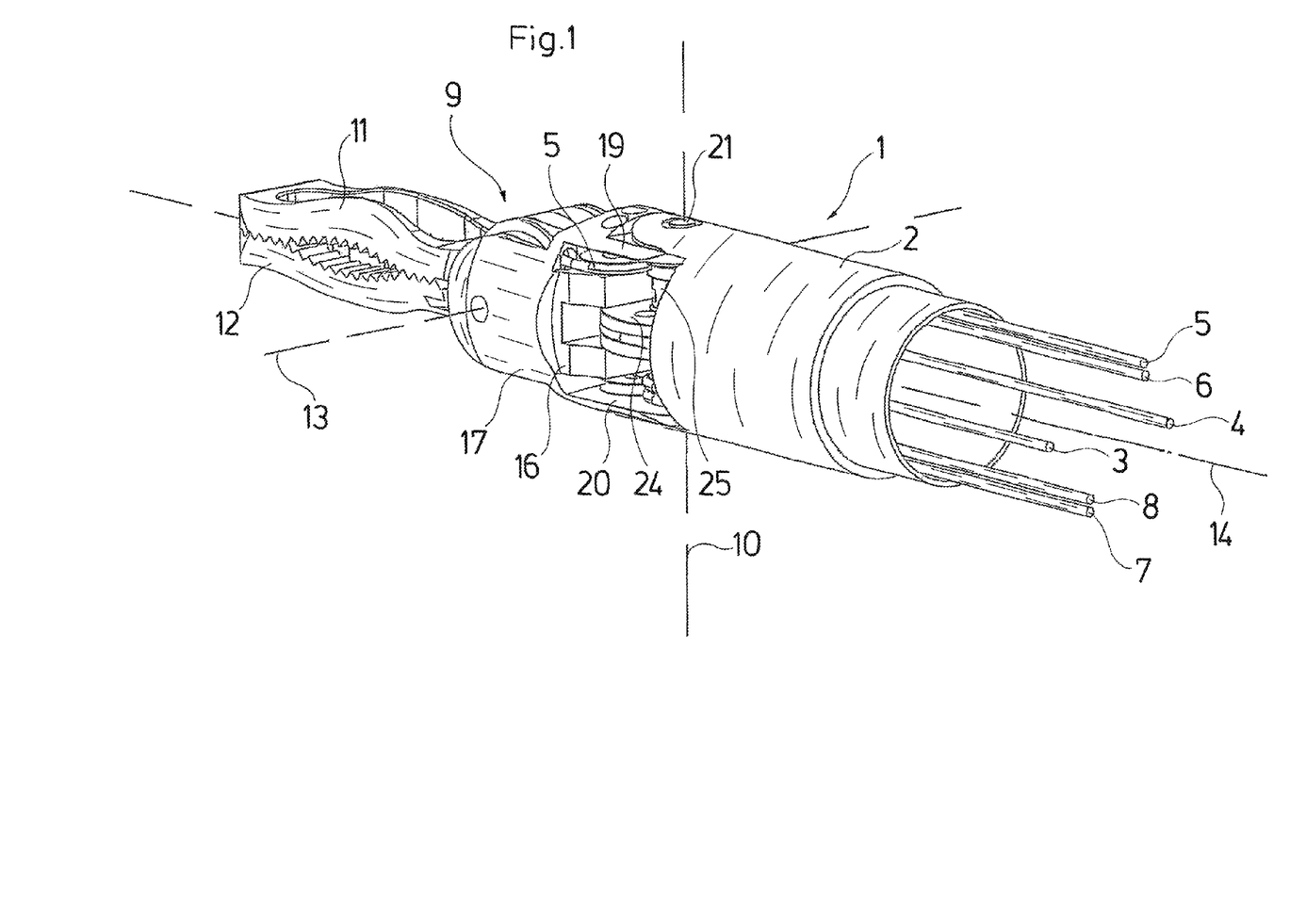
FIG. 1 is a simplified perspective representation showing the distal shank end with an instrument head and the pull means leading through the shank.
Figure 2:
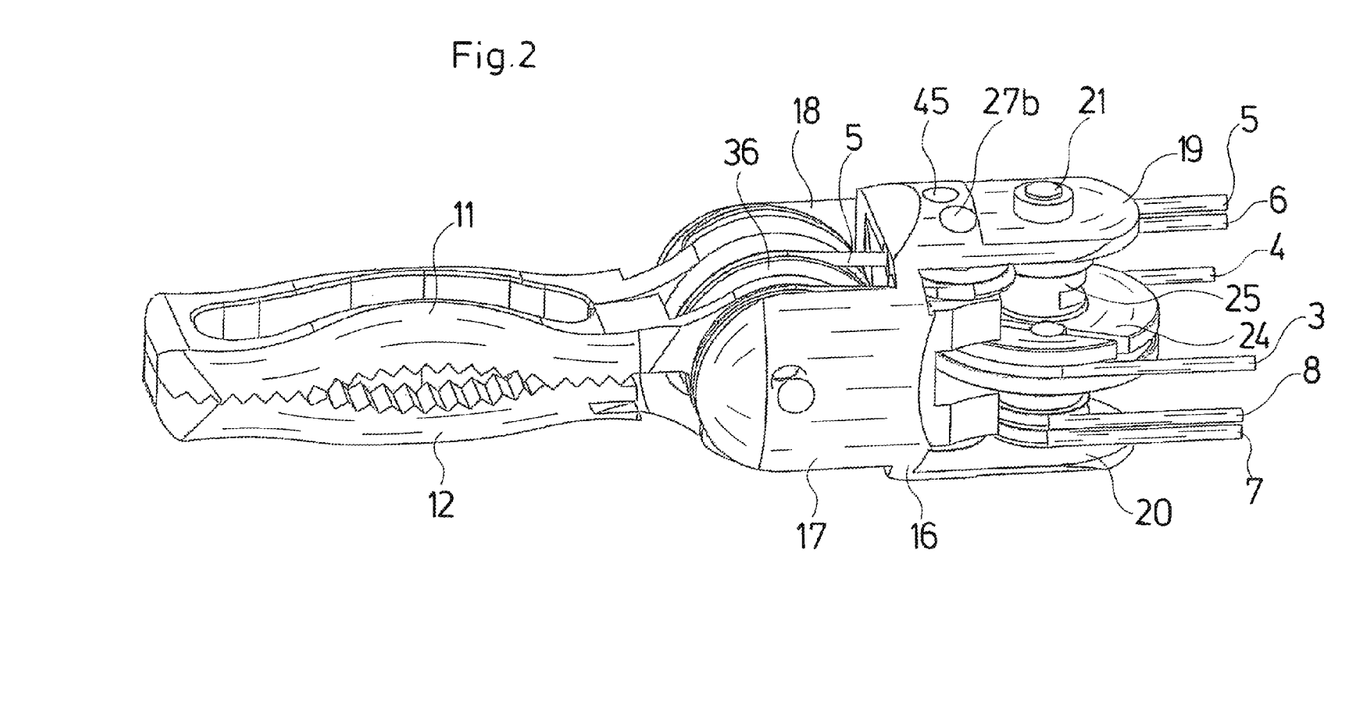
FIG. 2 is a perspective view of the distal instrument head without a shank.
Figure 3:
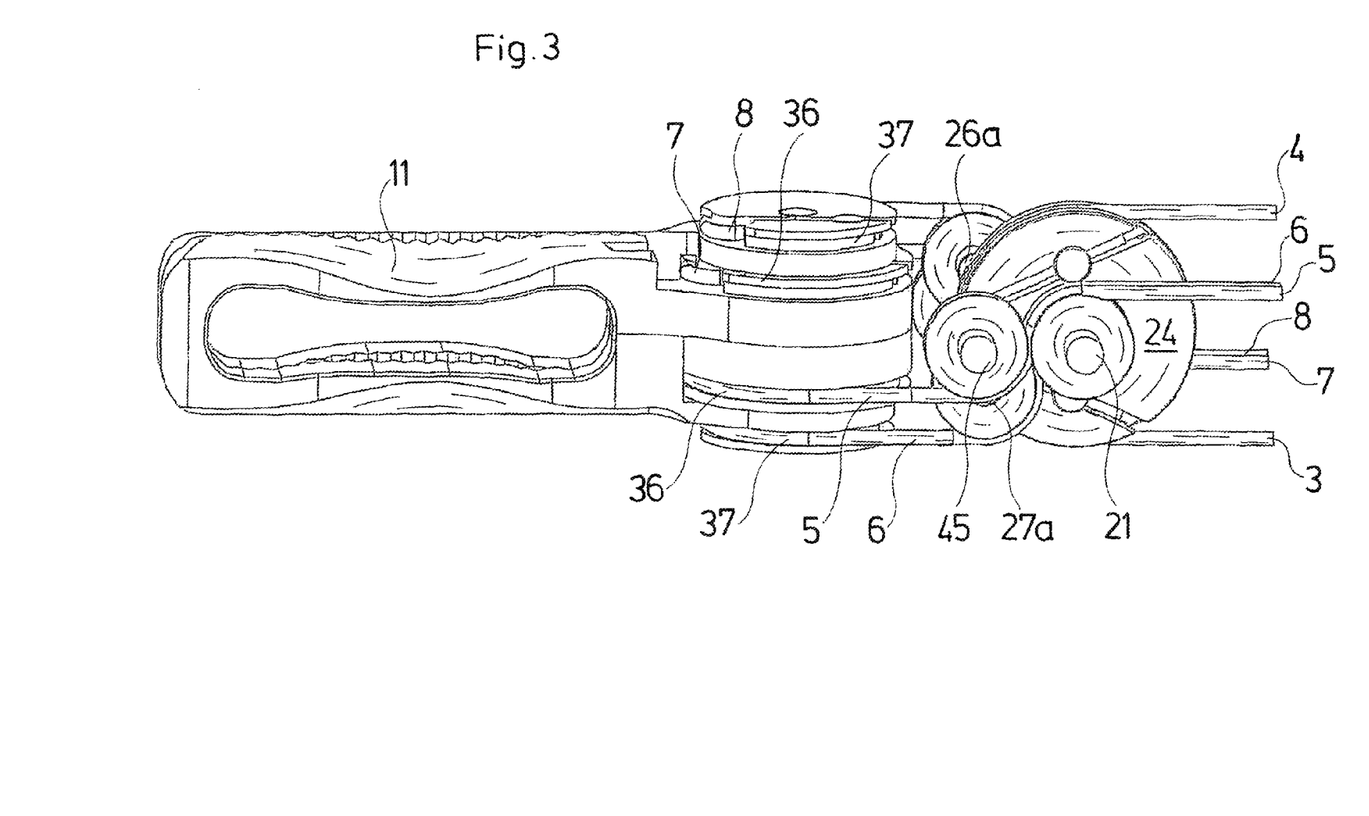
FIG. 3 is a view of the instrument head without an intermediate piece and shank.
Figure 4:
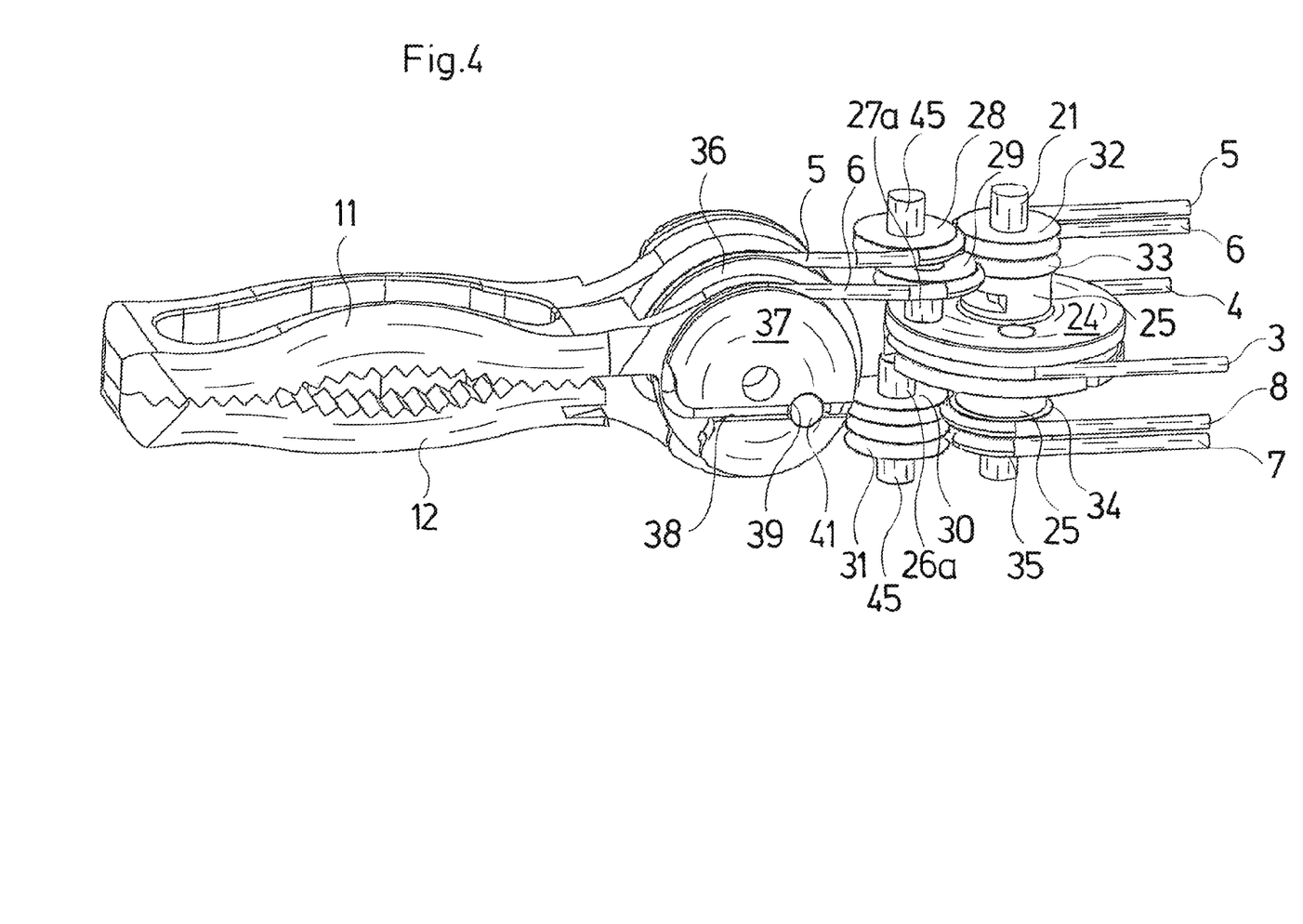
FIG. 4 is a representation which is rotated by 90° about the longitudinal axis compared to FIG. 3.

Shown in FIG. 1 is the distal shank end 1 as well as the pull means led through the shank 2, in the form of pull wires 3-8 which are led through the shank 2 up to the proximal end and are fastened there via levers, rollers or likewise, for the purpose of applying pull forces. Thereby, the pull wires 3 and 4 serve for pivoting the instrument head 9 about a pivot axis 10, with respect to the distal shank end 1. The pull wires 5 and 6 serve for pivoting the jaw part 11 of a forceps jaw which is at the top in FIG. 1, wherein the jaw part 12 of this forces jaw which is at the bottom in FIG. 1 can be controlled in its pivot movement by the pull wires 7 and 8. The jaw parts 11 and 12 are pivotable about a common axis 13 which with respect to the instrument axis 14 is arranged at a distance and rotated by 90° to the pivot axis 10.

All details made hereinafter with respect to the longitudinal axis 14 of the instrument relate to the nonangled arrangement of the instrument head 9 as well as of the jaw parts 11 and 12, said arrangement being represented in FIG. 1.

The instrument head 9 comprises an intermediate piece 15 which is constructed of a base body 16 which is circularly round in its outer contour. Two limbs 17 and 18 which are offset by 180° with respect to the longitudinal axis 14 and between which the jaw parts 11 and 12 are pivotably mounted extend distally from the intermediate piece, and two likewise diametrically arranged limbs 19 and 20 which are arranged offset to one another by 180° with respect to the axis 14 and which are offset by 90° to the limbs 17 and 18 with respect to the axis 14 extend proximally from the intermediate piece. The limbs 17 and 18 as well as the limbs 19 and 20 are arranged close to the outer periphery of the base body 16 and continue the shank shape of the shank 2 which is circularly round in cross section, to the outside in these regions.

Figure 12:
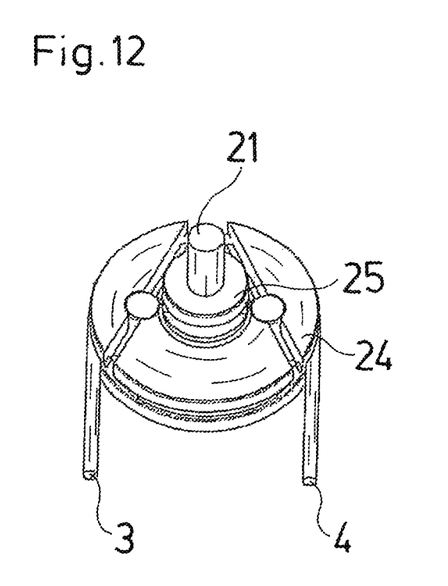
FIG. 12 is a perspective representation showing the curved disk with shaft and pull elements for the pivoting movement of the instrument head.
Figure 13:
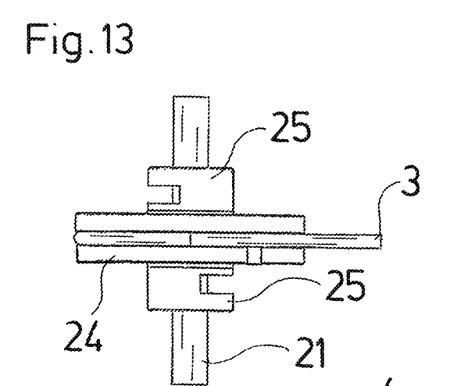
FIG. 13 is a lateral view, transverse to the pivot axis of the components, according to FIG. 12.
Figure 14:
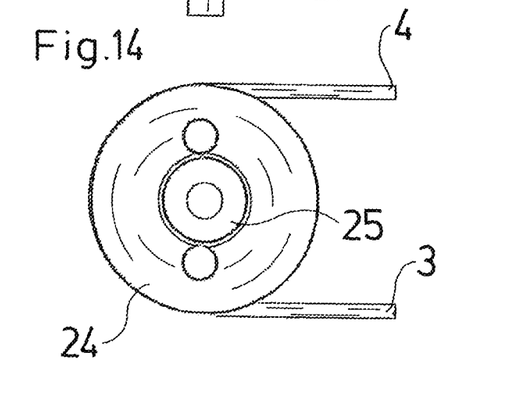
FIG. 14 is a lateral view in the direction of the pivot axis.

The limbs 19 and 20 are connected in a rotatably fixed manner to the shaft 21 which is rotatably mounted in recesses of limbs provided at the distal end of the shank 2. A curved disk 24 is fastened on the shaft 21 in a rotationally fixed manner, and pull wires 3 and 4 run over this curved disk and are each fixed with their ends laterally in the disc. The shaft 21 laterally of the curved disk 24 yet comprises two spacer discs 25 which in the described embodiment are designed as one piece with the curved disk 24 and the shaft 21, but which can however also be rotatably seated on the shaft 21 in the manner of a washer. In this context, it is particularly the representations in the FIGS. 12-14 which are referred to, where this is shown in detail.

Figure 11:
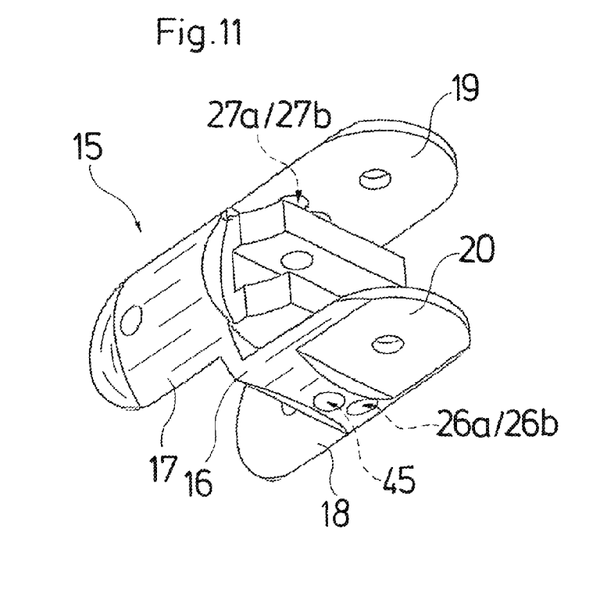
FIG. 11 is an enlarged perspective representation showing the intermediate piece.

The proximally pointing limbs 19 and 20 of the intermediate piece 15 in the region between the shaft 21 and the base body 16 yet comprise three parallel pivots, specifically a short pivot 45 offset at a distance and parallel to the shaft 21, as well as two likewise short pivots 26a and 27a which are arranged laterally offset thereto in each case. The pivots 45, 26a and 27a are arranged parallel to the shaft 21, and the central pivots 45 lie behind the shaft 21 seen in the direction of the longitudinal axis of the instrument 14. The bores for the short pivots 26a and 27a are closed off to the outside by blind pins 26b and 27b respectively. As to the bores, in which the short pivots 26a and 27a as well as 45 are integrated in the intermediate piece 15, is indicated by way of FIG. 11 by interrupted lines. Thereby, firstly the short pivot 26a for example is to be inserted into the respective bore and this is then to be closed by the blind pin 26b, as on the other side the short pivot 27a is firstly to be inserted and then to be closed by the blind pin 27b.

The central pivots 45 carry two deflection rollers 28 and 29 and the short pivots 26a and 27a in each case carry a deflection roller 30 and 31 respectively. The deflection rollers 28-31 are constructionally identical and are freely rotatably mounted and serve for the deflection of the pull wires 5-8 and interact with further, four constructionally identical deflection rollers 32-35 which are rotatably mounted in each case in pairs on the shaft 21, laterally of the spacer discs 25. Thereby, a roller pair each consisting of one of the deflection rollers 28-31 as well one of the rollers 32-35 arranged on the shaft 21 is formed for each of the pull wires 5-8. Each roller pair is arranged such that the wrap angle of a pull wire about a roller pair is always constant independently of the pivot position of the instrument head 9 to the shank 2, i.e. the wrap angle of the deflection roller 28-31 increases by the corresponding extent to which the wrap angle of an associated deflection roller 32-35 seated on the shaft 21 reduces, and vice versa. This arrangement has the effect that the position of the pull wires 5-8 with respect to the pivot position of the jaw parts 11 and 12 connected thereto, about the axis 13, is independent of the pivot position of the instrument head 9 about the pivot axis 10.

The forceps jaw parts 11 and 12 are freely movably mounted about the rotation axis 13 and are in each case connected to two pull wires 5 and 6 or 7 and 8 respectively, wherein one pull wire is provided for pivoting a jaw part in the opening direction and the other pull wire is provided for pivoting the jaw part in the closure direction. The jaw parts 11 and 12 not only can be pivoted to one another and away from one another, but also pivoted together since two pull wires 5 and 6 or 7 and 8 are assigned to each jaw part 11 and 12 respectively, so that the tool can also grip in a direction different to the longitudinal direction 14.

For this, each jaw part is connected to two curved disks, specifically to a large curved disk 36 arranged close to the longitudinal middle axis 14, and a smaller curved disk 37 arranged next to this. The large curved disk 36 has a significantly larger radius than the small curved disk 37. Both curved disks are designed and arranged such in the straight condition represented in FIG. 1, with a closed forceps jaw, they are wrapped by a pull wire 5-8 by more than 90°. They comprise a lateral recess 38 which runs roughly in the extension of the forceps jaw, is designed in a channel-like manner and is provided for receiving a pull cable end. A bore 39, in which a transverse pin 41, in which the pull cable end is fastened, is arranged transversely to this.

Figure 5:
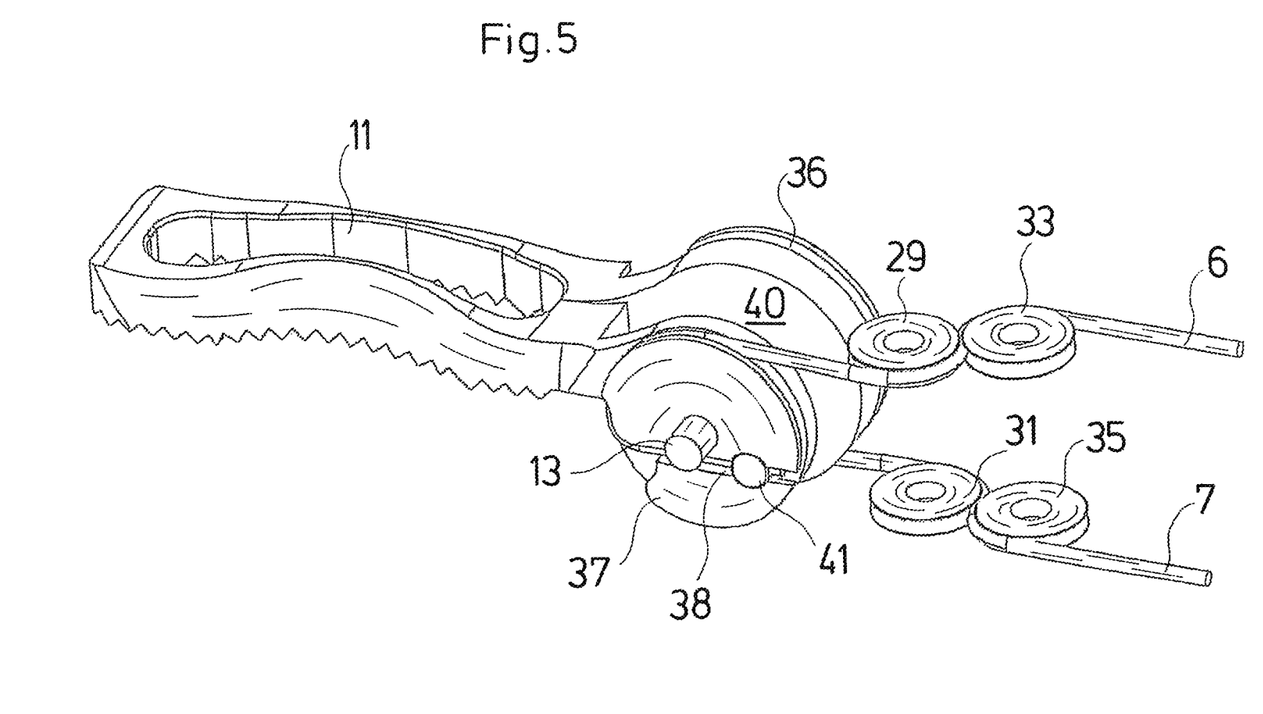
FIG. 5 is a schematic representation showing the upper jaw part in FIG. 1, with the pull means connected thereto.
Figure 6:
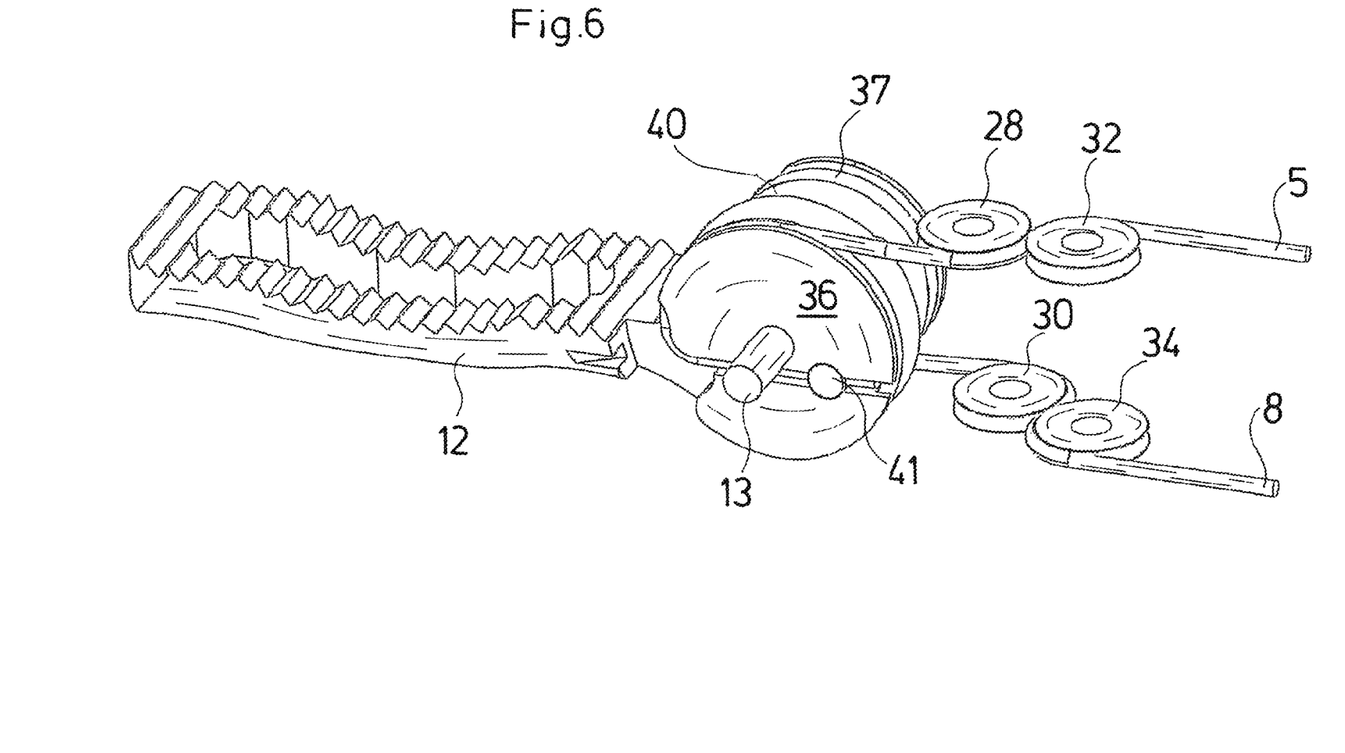
FIG. 6 is a view showing the lower jaw part represented in FIG. 1, with the pull means connected thereto.

With the represented embodiment, pull wires which move the respective forceps jaw part 11 and 12 onto the other forceps jaw part 12 and 11, i.e. affect the jaw part in the closure direction, are fastened on the large curved disks 36 which are arranged close to the longitudinal middle axis 14 roughly centrally between the limbs 17 and 18. The curved disks 37 which are smaller in diameter are connected to the pull wires of the jaw parts 11 and 12 which serve for opening the forceps jaw. By way of this arrangement, it is possible with the same pull force on the pull wires 5 and 6 or 7 and 8, to produce a higher force of the forceps jaw parts 11 and 12 in the closure direction of the jaw than in the opening direction, since a greater moment than with an equally large force transmission onto the smaller deflection discs 37 is produced on account of the larger radius of the large curved disks 36. As FIGS. 5 and 6 particularly illustrate, the large curved disks 36 lie to the inside, thus where the greatest free space within the shank contour is given with respect to the disc diameter, whereas the smaller curved disks 37 lie further to the outside, where there is less free space due to the curvature.

Figure 7:
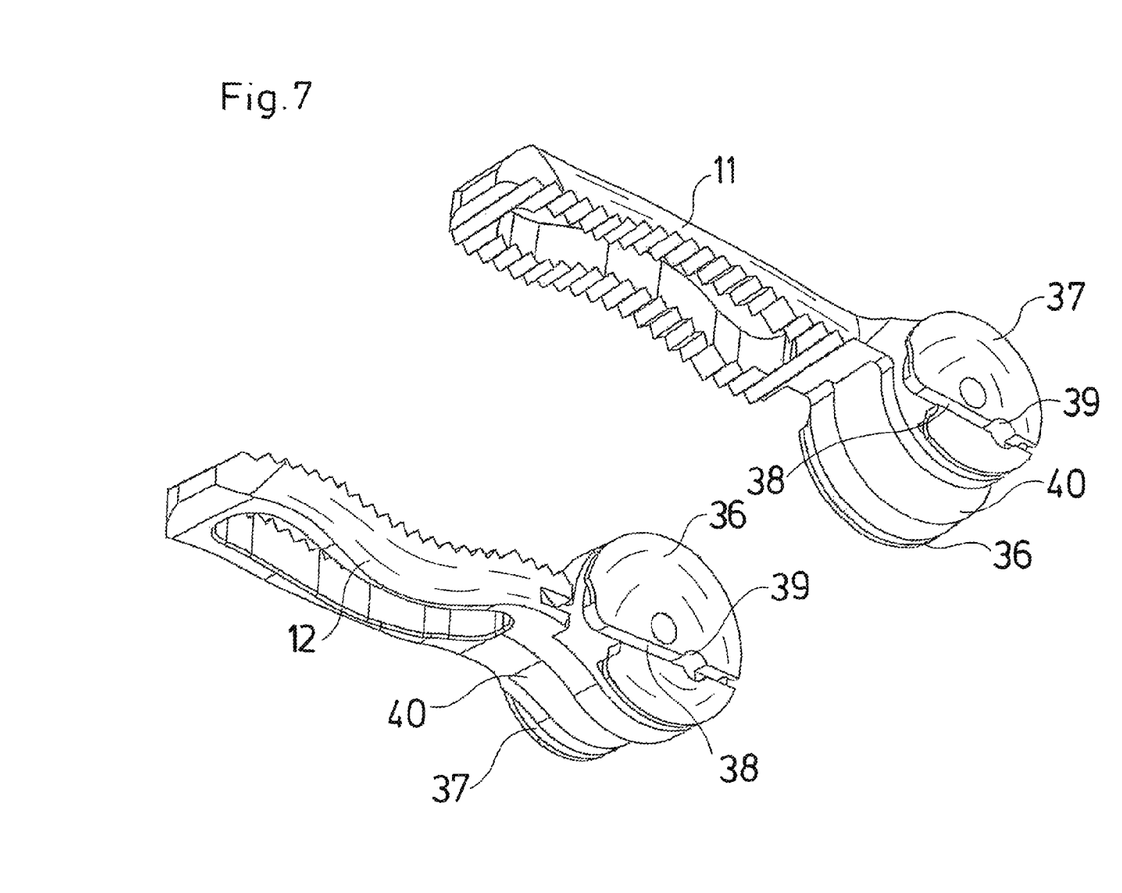
FIG. 7 is an exploded representation showing the two jaw parts.
Figures 8, 9, 10:
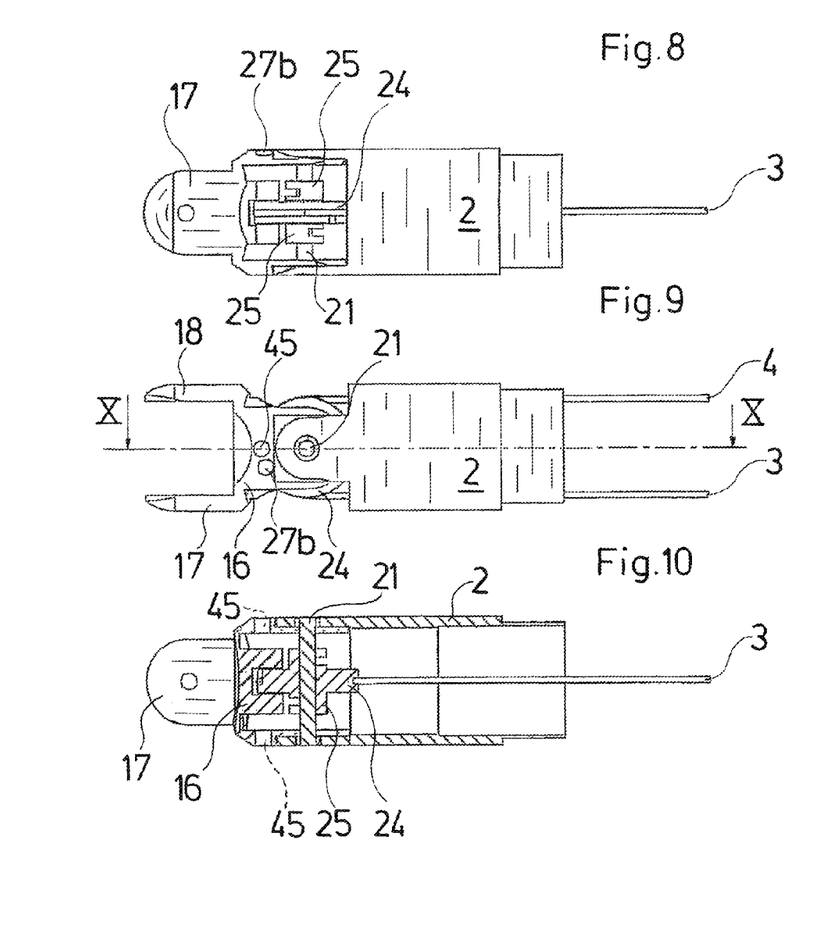
FIG. 8 is a view of the shank end with an intermediate piece without deflection rollers and jaw parts.
FIG. 9 is a view which is rotated by 90° with respect to FIG. 8.
FIG. 10 is a sectional view along the section line X-X in FIG. 9.

As FIG. 7 particularly illustrates, the jaw parts 11 and 12 with the associated curved disks 36 and 37 are designed identically in the represented embodiment example, i.e. two identical components can be used. Thereby, a free space 40 is formed between the large curved disk 36 and the smaller curved disk 37, in the region of the curved disks, and this free space is dimensioned such that on rotation of the component about 180° about the longitudinal axis, the large curved disk 36 of a jaw part 12 can be integrated between the two curved disks 36, 37 of the other jaw part 11. The two large curved disks 36 then each lie directly next to the longitudinal middle axis 14 and the smaller curved disks 37 next to this at a distance.

The instrument head described above can be pivoted about the axis 10 in two directions by way of applying a tensile force onto the pull wires 3 or 4. The forceps jaw can be opened by way of applying tensile or pull forces on the pull wires 6 and 8, and this forceps jaw is closed by way of applying tensile forces on the pull wires 5 and 7. If pull forces are simultaneously applied onto the pull wires 6 and 7 or 5 and 8, then the two jaw parts pivot in the same direction about the axis 13, without changing their angular position to one another.

While specific embodiments of the invention have been shown and described in detail to illustrate the application of the principles of the invention, it will be understood that the invention may be embodied otherwise without departing from such principles.

The invention claimed is:

1. An endoscopic instrument comprising:
a shank comprising a distal shank end;
an instrument head extending from said distal shank end, said instrument head comprising a tool, said tool comprising a longitudinal central axis, a first jaw part and a second jaw part, said first jaw part and said second jaw part being pivotable relative to each other;
a first member comprising a first disk peripheral edge and a first disk rotational axis, said first disk peripheral edge being located at a first radial distance from said first disk rotational axis;
a second disk comprising a second disk peripheral edge and a second disk rotational axis, said first disk and said second disk being connected to at least one of said first jaw part and second jaw part, said second disk rotational axis being aligned with said first disk rotational axis, said second disk peripheral edge being located at a second radial distance from said second disk rotational axis, said first radial distance being greater than said second radial distance, said first disk and said second member being associated with one of said first jaw part and said second jaw part for opening and closing said one of said first jaw part and said second jaw part, said first disk being located on one side of said one of said first jaw part and said second jaw part, said second disk being located on another side of said one of said first jaw part and said second jaw part, said first disk being located at a first distance from said longitudinal central axis, said second disk being located at a second distance from said longitudinal central axis, said first distance being less than said second distance; and
a plurality of pulling elements, at least a portion of each of said pulling elements extending in an interior of said shank, said first disk and said second disk being connected to one or more of said pulling elements, wherein actuation of said one or more pulling elements actuates said one of said first jaw part and said second jaw part.

2. An instrument according to claim 1, further comprising:
a third disk comprising a third disk peripheral edge and a third disk rotational axis, said third disk peripheral edge being located at a third radial distance from said third disk rotational axis;
a fourth disk comprising a fourth disk peripheral edge and a fourth disk rotational axis, said third disk and said fourth disk being connected to at least another one of said first jaw part and said second jaw part, said fourth disk rotational axis being aligned with said first disk rotational axis, said second disk rotational axis, said third disk rotational axis and said fourth disk rotational axis, said fourth disk peripheral edge being located at a fourth radial distance from said fourth disk rotational axis, said third radial distance being greater than said fourth radial distance, said third disk and said fourth disk being associated with another one of said first jaw part and said second jaw part for opening and closing said another one of said first jaw part and said second jaw part, said third disk being located on one side of said another one of said first jaw part and said second jaw part, said fourth disk being located on another side of said another one of said first jaw part and said second jaw part, said third disk being located at a third distance from said longitudinal central axis, said fourth disk being located at a fourth distance from said longitudinal central axis, said third distance being less than said fourth distance.

3. An instrument according to claim 2, wherein said first jaw part comprises a first jaw part first portion and a first jaw part second portion, said first jaw part first portion and said first jaw part second portion defining a first space, said second jaw part comprising a second jaw part first portion and a second jaw part second portion, said second jaw part first portion and said second jaw part second portion defining a second space, said first disk being located adjacent to one side of said first jaw part first portion, wherein another side of said first jaw part first portion defines at least a portion of said first space, said second disk being located adjacent to one side of said first jaw part second portion, wherein another side of said first jaw part second portion defines at least a portion of said first space, at least a portion of said first disk and at least a portion of said first jaw part first portion being arranged in said second space, wherein said first disk and said first jaw part first portion are located between said second jaw part first portion and said second jaw part second portion, said third disk being located adjacent to one side of said second jaw part first portion, wherein another side of said second jaw part first portion defines at least a portion of said second space, said fourth disk being located adjacent to one side of said second jaw part second portion, wherein another side of said second jaw part second portion defines at least a portion of said second space, at least a portion of said third disk and at least a portion of said second jaw part first portion being arranged in said first space, wherein said third disk and said second jaw part first portion are located between said first jaw part first portion and said first jaw part second portion.

* * * * *